United States Patent [19]

Harrison et al.

[11] 4,435,420

[45] Mar. 6, 1984

[54] ANTI-INFLAMMATORY AGENTS AND ANTIASTHMATIC AGENTS

[75] Inventors: Boyd L. Harrison; Niall S. Doherty, both of Cincinnati, Ohio

[73] Assignee: Merrell Dow Pharmaceuticals, Cincinnati, Ohio

[21] Appl. No.: 367,510

[22] Filed: Apr. 12, 1982

[51] Int. Cl.³ .................. A61K 31/385; C07C 339/06
[52] U.S. Cl. ...................................... 424/277; 549/38
[58] Field of Search ........................... 549/38; 424/277

[56] References Cited

U.S. PATENT DOCUMENTS 3,442,907  5/1969  Donche et al. ...................... 549/38
3,489,771  1/1970  Donche et al. ...................... 549/38
4,060,628  11/1977  Enders et al. ...................... 424/277
4,131,683  12/1978  Harrison et al. ................... 424/277
4,172,941  10/1979  Harrison et al. ..................... 544/28

OTHER PUBLICATIONS

Nakai et al., Tetrahedron Letters, 39 (1967) pp. 3835–3838.

Primary Examiner—Richard Raymond
Attorney, Agent, or Firm—John J. Kolano; Gary D. Street; Raymond A. McDonald

[57] ABSTRACT

N-(1,3-dithiolan-2-ylidene)-4-alkylanilines are useful as anti-inflammatory agents, as analgesic agents and as antiasthmatic agents. The compounds involved can be prepared by the reaction of an appropriate 4-alkylaniline with a methyl(1,3-dithiolan-2-ylidene)sulfonium salt or with carbon disulfide and ethylene dibromide in the presence of a base.

12 Claims, No Drawings

ANTI-INFLAMMATORY AGENTS AND ANTIASTHMATIC AGENTS

N-(1,3-dithiolan-2-ylidene)aniline and some closely related compounds have been described in the literature for various purposes but there has been no indication of pharmacological activity. U.S. Pat. No. 4,131,683 describes 1,3-dithiolan-2-ylideneamino substituted phenylactic acids and describes their utility for a number of purposes, including their use as anti-inflammatory agents. It has now been found, surprisingly, that the carboxylic acid function is not necessary for anti-inflammatory activity in such compounds and simple alkylphenyl compounds are active anti-inflammatory agents. Such compounds are also useful as antiasthmatic agents and analgesic agents.

Thus, the present invention is directed to methods of treatment using certain N-(1,3-dithiolan-2-ylidene)anilines which have the following structural formula

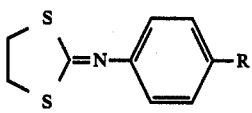

wherein R is a straight or branched-chain alkyl of 1-10 carbon atoms or cycloalkyl of 5-7 carbon atoms; and the pharmaceutically acceptable acid addition salts of those compounds.

Examples of the alkyl groups referred to above are propyl, isopropyl, butyl, isobutyl, hexyl, octyl, and decyl. The examples of the cycloalkyl groups are cyclopentyl, cyclohexyl and cycloheptyl.

The pharmaceutically acceptable acid addition salts are equivalent to the aforesaid amines for the purposes of this invention. Illustrative of such salts are salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and 4-toluenesulfonic acid.

With regard to the methods of treatment of the present invention, the compounds as described in the structural formula above are useful as antiasthmatic agents and analgesic agents. Those compounds wherein R is alkyl of 3-10 carbon atoms are particularly preferred for use as anti-inflammatory agents. The compounds wherein R is alkyl of 6-10 carbon atoms are further especially preferred as anti-inflammatory agents. As anti-inflammatory agents, the above compounds are useful in the treatment of painful inflammation conditions such as rheumatoid arthritis or osteoarthritis or also dental, post-operative and trauma-induced pain. The compounds are also useful in the treatment of dysmenorrhea.

As examples of compounds useful in the present invention are the following:
N-(1,3-dithiolan-2-ylidene)-4-pentylaniline.
N-(1,3-dithiolan-2-ylidene)-4-heptylaniline.
N-(1,3-dithiolan-2-ylidene)-4-decylaniline.
N-(1,3-dithiolan-2-ylidene)-4-isobutylaniline.
N-(1,3-dithiolan-2-ylidene)-4-(1-methylpropyl)aniline.
N-(1,3-dithiolan-2-ylidene)-4-(2-methylhexyl)aniline.
4-Cyclopentyl-N-(1,3-dithiolan-2-ylidene)aniline.
4-Cycloheptyl-N-(1,3-dithiolan-2-ylidene)aniline.

The compounds used in the present invention are conveniently obtained by the reaction of methyl(1,3-dithiolan-2-ylidene)sulfonium iodide with a 4-alkylaniline of the formula

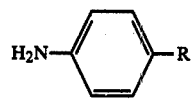

wherein R is defined as above. The reaction is carried out at room temperature in the presence of a tertiary amine such as triethylamine and using an inert solvent such as dimethylformamide.

Alternatively, the alkylaniline referred to above can be reacted with carbon disulfide and an alkali metal base such as potassium carbonate to give the corresponding alkali metal dithiocarbamate which is then reacted with ethylene dibromide to give the desired dithiolane. Actually, the dithiocarbamate is not isolated from the reaction mixture but it is simply further reacted with the ethylene dibromide. The entire reaction is carried out in an inert solvent such as dimethylformamide.

The procedure described above will ordinarily give the product as the free base and this can be converted to the corresponding salt by standard procedures.

The activity of the compounds as anti-inflammatory agents was determined by the following procedure. Groups of male Sprague-Dawley rats were starved overnight before dosing with the test compounds. One (1) hour after dosing, 0.05 ml of 1% carrageenan was injected into the left-hind paw and swelling was measured three (3) hours later. Animals were then autopsied and the stomachs were examined for the presence of ulcers. The compounds above wherein R is alkyl of 3-10 carbon atoms were found to be active in this test and, surprisingly, the animals showed little or no stomach ulceration.

Anti-inflammatory activity was further demonstrated by the adjuvant arthritis test in the rat. Arthritis was induced by injection of heat-killed Mycobacterium turberculosis into the tail of Sprague-Dawley rats. When the disease had fully developed fifteen (15) days later, the animals were weighed, the hind-paw volumes determined and dosing commenced. After eight (8) daily doses of test compound, the measurements were repeated and the changes in the parameters over the dosing period were recorded. The procedure involved is a demonstration of anti-inflammatory activity on prolonged dosing and those compounds wherein R is alkyl of 6-10 carbon atoms are particularly active in this test.

Analgesic activity for the present compounds was demonstrated by the acetic acid writhing test. The method was a modification of the procedure of Whittle [Brit. J. Pharmacol., 22, 246 (1964)]. Groups of 5 to 10 mice were administered one or more doses of test compound by the route desired (except intraperitoneal). At a selected time thereafter, acetic acid (0.4 ml of a 0.25% v/v solution) was administered intraperitoneally to the mice. Starting 5 minutes later, the animals were observed for a period of 15 minutes for the appearance of abdominal writhing and the number of squirms for each mouse was counted. Analgesia was considered significant in those mice which did not squirm during the 15 minute observation period. To determine the $ED_{50}$, 4 or more doses were tested in groups of 10 mice. The compounds of the present invention were active when tested by the above procedure.

Utility of the present compounds as antiasthmatic agents was demonstrated by their inhibition of SRS biosynthesis. Specifically, rat peritoneal cells were incubated at 37° C. in Hanks' balanced-salt solution containing indomethacin (1/µ/ml) and various concentrations of test compounds for thirty (30) minutes before adding calcium ionophore. After a further fifteen (15) minutes of incubation, the reaction was stopped, and the SRS was extracted and bioassayed. The indomethacin was present during the incubation to block formation of prostaglandins which could interfere with the bioassay. When tested by the above procedure, all of the compounds of the present invention were found to be active.

The anti-inflammatory, analgesic and antiasthmatic agents of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The compositions used may be in the form of tablets, capsules, dragees, gelules, granules, suppositories, injectable solutions or suspensions, pomades, creams, gels and aerosol prepartions formed in the usual fashion. Examples of suitable excipients are talc, gum arabic, lactose, starch, magnesium stearate, cacao butter, aqueous and non-aqueous vehicles, fatty bodies of animal or vegetable origin, paraffinic derivatives, glycols, diverse wetting agents, dispersants and emulsifiers and preservatives.

The novel methods of the invention for treating inflammation, pain and asthma in mammals comprise administering to warm-blooded animals an effective amount of at least one compound of the invention. The dosage administered will, of course, vary depending upon known factors such as the pharmacodynamic characteristics of the particular agent, and its mode and route of administration; age, health and weight of the recipient; nature and extent of the symptoms, kind of concurrent treatment, frequency of treatment, and the effect desired. Usually, for anti-inflammatory purposes, a daily dosage of active ingredient can be about 0.5 to 500 milligrams and preferably 5 to 100 milligrams per kilogram of body weight per day in the adult by the oral route. The active ingredient can be given in a single daily dose, in divided doses 2 to 4 times a day, or in sustained release form to obtain the desired results.

The compositions of specific illustrative dosage units for pharmaceutical formulations which may be employed in practicing the present invention are given below. Standard procedures are used in the preparation of the individual formulations. Similar formulations can also be prepared using appropriate quantities of the active ingredients or other active ingredients.

| | Amount |
|---|---|
| Capsule | |
| (a) N—(1,3-dithiolan-2-ylidene)-4-hexylaniline dihydrogen sulfate | 100 mg |
| (b) microcrystalline cellulose | 30 mg |
| (c) magnesium stearate | 2 mg |
| Tablet | |
| (a) N—(1,3-dithiolan-2-ylidene)-4-hexylaniline dihydrogen sulfate | 100 mg |
| (b) microcrystalline cellulose | 30 mg |
| (c) starch glycolate sodium | 4 mg |
| (d) polyvinylpyrrolidone | 5 mg |
| (e) magnesium stearate | 2 mg |
| Suppository | |
| (a) N—(1,3-dithiolan-2-ylidene)-4-hexylaniline dihydrogen sulfate | 50 mg |
| (b) Polyethylene glycol 1000 | 1350 mg |
| (c) Polyethylene glycol 4000 | 450 mg |

The polyethylene glycols are melted and mixed, the active ingredient is then suspended and the resultant mixture is then molded to give appropriate dosage units.

The following examples are set forth to illustrate the preparation of compounds employed in the present invention but should not be construed as limiting it in any way.

EXAMPLE 1

A solution was prepared from 2.83 g of 4-hexylaniline and 100 ml of dimethylformamide and 4 g of triethylamine was added. Then, all at once, 4.9 g of methyl(1,3-dithiolan-2-ylidene)sulfonium iodide was added. This dissolved slowly to give a pale-yellow solution which was allowed to stir at room temperature under argon for 1 hour. It was then poured into an equal volume of water and extracted 3 times with diethyl ether. The combined ether extracts were washed with 0.2 N hydrochloric acid until thin-layer chromatography showed that residual 4-hexylaniline had been removed. The ether solution was then washed once with aqueous saturated sodium bicarbonate solution, 3 times with water, and once with saturated aqueous sodium chloride solution and then dried over anhydrous magnesium sulfate. The solution was then filtered and the solvent was evaporated under reduced pressure. Methylene chloride was added to the residue and evaporation was repeated to leave a crude yellow oil. The product thus obtained was N-(1,3-dithiolan-2-ylidene)-4-hexylaniline and it has the following structural formula

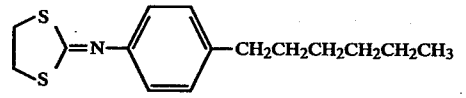

EXAMPLE 2

The crude product obtained in Example 1 was dissolved in 200 ml of anhydrous diethyl ether and a solution of 1.57 g of concentrated sulfuric acid in 100 ml of anhydrous diethyl ether was added dropwise at room temperature. A white precipitate formed immediately and, after the addition was complete, the mixture was cooled to −20° C. and filtered cold, and the separated solid was washed with cold diethyl ether. The solid was air dried and recrystallized from hot acetone to give N-(1,3-dithiolan-2-ylidene)-4-hexylaniline dihydrogen sulfate as shiny white platelets melting at about 145°–146° C.

EXAMPLE 3

If the procecure of Example 1 was repeated using methyl(1,3-dithiolan-2-ylidene)sulfonium iodide and the appropriate 4-substituted aniline, the following compounds were obtained:

4-Cyclohexyl-N-(1,3-dithiolan-2-ylidene)aniline melting at about 138.5°–139.5° C. after recrystallization from a mixture of toluene and hexane.

4-(t-Butyl)-N-(1,3-dithiolan-2-ylidene)aniline melting at about 73.5°–74.5° C. after recrystallization from hexane.

EXAMPLE 4

The procedure of Example 1 was repeated using methyl(1,3-dithiolan-2-ylidene)sulfonium iodide and the appropriate 4-alkyl substituted aniline. The product obtained in this was was then reacted with sulfuric acid as described in Example 2, to give the following compounds:

N-(1,3-Dithiolan-2-ylidene)-4-methylaniline dihydrogen sulfate melting at about 203.5°–204.5° C. after recrystallization from acetic acid.

N-(1,3-Dithiolan-2-ylidene)-4-propylaniline dihydrogen sulfate melting at about 156°–157.5° C. after recrystallization from acetone.

EXAMPLE 5

Methyl(1,3-dithiolan-2-ylidene)sulfonium iodide was reacted with the appropriate 4-alkyl substituted aniline according to the procedure described in Example 1. The crude product obtained was purified by chromatography on silica gel using ethyl acetate/hexane and the product thus obtained was reacted with sulfuric acid according to the method described in Example 2 to give the following compounds:

N-(1,3-dithiolan-2-ylidene)-4-ethylaniline dihydrogen sulfate melting at about 174.5°–175.5° C. after recrystallization from a mixture of acetone and methanol.

N-(1,3-dithiolan-2-ylidene)-4-isopropylaniline dihydrogen sulfate melting at about 96.5°–98.5° C. after recrystallization from acetone.

N-(1,3-dithiolan-2-ylidene)-4-octylaniline dihydrogen sulfate melting at about 139.5°–180° C. after recrystallization from acetone.

4-Butyl-N-(1,3-dithiolan-2-ylidene)aniline, salt with 4-toluenesulfonic acid, melting at about 93°–95° C. after recrystallization from a mixture of chloroform and ether. In this case, 4-toluenesulfonic acid was used in place of sulfuric acid in the preparation of the salt.

EXAMPLE 6

A solution of 1.77 g of 4-hexylaniline in 20 ml of dried dimethylformamide containing 2.76 g of potassium carbonate was prepared and 0.84 g of carbon disulfide was added. The mixtue was allowed to stir at room temperature and its first became yellow and then yellow-orange. After about 1 hour, a solution of 2.26 g of 1,2-dibromoethane in 5 ml of dimethylformamide was added dropwise to the stirred solution. After this addition, the color of the solution began changing to light yellow and a fine precipitate began to form. After 2 hours at room temperature, an additional 0.84 g of carbon disulfide was added all at once and the mixture was stirred for an additional 3 hours. Then, 2.26 g of 1,2-dibromoethane was added and the mixture was stirred for an additional 20 hours. The reaction mixture was poured into water and the resultant aqueous mixture was extracted 3 times with diethyl ether. The combined ether extracts were washed with 0.2 N hydrochloric acid, water, and aqueous saturated sodium chloride solution and then dried over magnesium sulfate. The solvent was then evaporated, methylene chloride was added, and the solvent was again evaporated to leave and orangish oil which was crude N-(1,3-dithiolan-2-ylidene)-4-hexylaniline.

The crude product obtained above was dissolved in 150 ml of anhydrous diethyl ether and to the resultant yellowish solution was added dropwise 1.0 g of sulfuric acid in 75 ml of diethyl ether. A solid began to precipitate immediately. When the addition was completed, the resultant mixture was placed in a freezer for 1 hour. The precipitate was then separated by filtration, washed well with diethyl ether, and dried under reduced pressure. The off-white solid obtained was recrystallized by dissolving it in 375 ml of hot acetone, filtering the solution through a coarse fritted funnel, concentrating it to about 200 ml, and then cooling. After crystallization had occurred at room temperature, the mixture was then placed in a freezer to complete crystallization. The solid was then separated by filtration, washed with cold acetone and dried to give N-(1,3-dithiolan-2-ylidene)-4-hexylaniline dihydrogen sulfate as white platelets.

EXAMPLE 7

A solution was prepared from 13.6 g of 1,3-dithiolane-2-thione (ethylenetrithiocarbonate) in 25 ml of reagent nitromethane and 14.2 g of methyl iodide was added dropwise at room temperature with stirring under an atmosphere of nitrogen. The reaction mixture was wrapped with foil for protection from light and stirring was continued for 16 hours. The crystals that formed were separated by filtration, washed with dry benzene and dried in vacuo to give methyl(1,3-dithiolan-2-ylidene)sulfonium iodide as brown crystals melting at about 80°–83° C.

What is claimed is:

1. A method of treating asthma which comprises administering to a patient in need thereof an effective antiasthmatic amount of a compound of the formula:

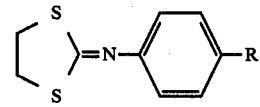

wherein R is alkyl of 1–10 carbon atoms or cycloalkyl of 5–7 carbon atoms; and the pharmaceutically acceptable acid addition salts thereof.

2. A method of treating asthma according to claim 1 which comprises administering N-(1,3-dithiolan-2-ylidene)-4-hexylaniline.

3. A method of treating asthma according to claim 1 which comprises administering 4-cyclohexyl-N-(1,3-dithiolan-2-ylidene)aniline.

4. A method of treating inflammation which comprises administering to a patient in need thereof an effective anti-inflammatory amount of a compound of the formula:

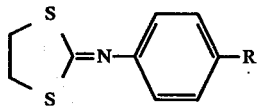

wherein R is alkyl of 3–10 carbon atoms, and the pharmaceutically acceptable acid addition salts thereof.

5. A method of treating inflammation according to claim 4 which comprises administering an effective anti-inflammatory amount of 4-butyl-N-(1,3-dithiolan-2-ylidene)aniline.

6. A method of treating inflammation according to claim 4 which comprises administering an effective anti-inflammatory amount of a compound of the formula:

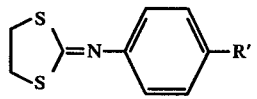

wherein R' is alkyl of 6–10 carbon atoms, and the pharmaceutically acceptable acid addition salts thereof.

7. A method of treating inflammation according to claim 4 which comprises administering an effective anti-inflammatory amount of N-(1,3-dithiolan-2-ylidene)-4-hexylaniline.

8. A method of treating inflammation according to claim 4 which comprises administering an effective amount of N-(1,3-dithiolan-2-ylidene)-4-octylaniline.

9. A compound of the formula:

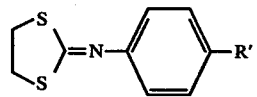

wherein R' is alkyl of 6–8 carbon atoms; and the pharmaceutically acceptable acid addition salts thereof.

10. A compound according to claim 9 which is N-(1,3-dithiolan-2-ylidene)-4-hexylaniline.

11. A compound according to claim 9 which is N-(1,3-dithiolan-2-ylidene)-4-hexylaniline dihydrogen sulfate.

12. A compound according to claim 9 which is N-(1,3-dithiolan-2-ylidene)-4-octylaniline.

* * * * *